(12) United States Patent
Yang et al.

(10) Patent No.: US 9,767,373 B2
(45) Date of Patent: Sep. 19, 2017

(54) HEAD-MOUNTED DISPLAY HEAD POSE AND ACTIVITY ESTIMATION

(71) Applicant: Ford Global Technologies, LLC, Dearborn, MI (US)

(72) Inventors: Hsin-hsiang Yang, Ann Arbor, MI (US); Kwaku O. Prakah-Asante, Commerce Township, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 109 days.

(21) Appl. No.: 14/478,440

(22) Filed: Sep. 5, 2014

(65) Prior Publication Data

US 2016/0070966 A1    Mar. 10, 2016

(51) Int. Cl.
| | |
|---|---|
| *G06K 9/00* | (2006.01) |
| *G02B 27/01* | (2006.01) |
| *A61B 5/11* | (2006.01) |
| *B60W 40/08* | (2012.01) |
| *B60R 21/015* | (2006.01) |

(Continued)

(52) U.S. Cl.
CPC ............ *G06K 9/00845* (2013.01); *A61B 5/11* (2013.01); *A61B 5/1116* (2013.01); *B60R 21/01542* (2014.10); *B60W 40/08* (2013.01); *G02B 27/0093* (2013.01); *G02B 27/017* (2013.01); *G06F 3/012* (2013.01); *G06K 9/00335* (2013.01); *B60R 21/01552* (2014.10); *B60W 2040/0827* (2013.01); *G02B 2027/014* (2013.01); *G02B 2027/0141* (2013.01); *G02B 2027/0178* (2013.01); *G02B 2027/0187* (2013.01)

(58) Field of Classification Search
None
See application file for complete search history.

(56) References Cited

U.S. PATENT DOCUMENTS 6,091,334 A * 7/2000 Galiana .................. G08B 21/06
340/439
6,724,920 B1 * 4/2004 Berenz ............... G06K 9/00221
180/169

(Continued)

OTHER PUBLICATIONS

VRGuy, Columbia, MD, USA, May 26, 2013, "What you should know about Head Trackers." (4 pages).

*Primary Examiner* — Dismery Mercedes
(74) *Attorney, Agent, or Firm* — Franklin A. MacKenzie; Brooks Kushman P.C.

(57) ABSTRACT

A system may receive head pose indications determined according to movement data from a motion sensor of an optical head-mounted display worn by a vehicle driver, determine, according to the head pose indications, driver activity characteristics indicative of a history of movement of the head of the driver, and send the driver activity characteristics to a driver-aware vehicle system configured to adjust driver notification based on the driver activity characteristics. The system may also receive raw movement data from a motion sensor of an optical head-mounted display worn on a head of a vehicle driver, compute head velocity data based on the raw movement data, compute head displacement data based on the head velocity data, and update head pose indications indicative of head positioning upon determining that the head displacement data exceeds a predetermined threshold displacement.

16 Claims, 7 Drawing Sheets

(51) Int. Cl.
*G06F 3/01* (2006.01)
*G02B 27/00* (2006.01)

(56) References Cited

U.S. PATENT DOCUMENTS

| | | | | |
|---|---|---|---|---|
| 7,394,393 | B2* | 7/2008 | Zhang | B60W 40/09 |
| | | | | 340/573.1 |
| 7,460,940 | B2* | 12/2008 | Larsson | A61B 3/113 |
| | | | | 180/272 |
| RE41,376 | E* | 6/2010 | Torch | A61B 3/0066 |
| | | | | 340/573.1 |
| 8,487,775 | B2* | 7/2013 | Victor | A61B 3/113 |
| | | | | 180/272 |
| 8,604,932 | B2* | 12/2013 | Breed | B60J 10/00 |
| | | | | 340/576 |
| 8,690,750 | B2 | 4/2014 | Krueger | |
| 8,706,170 | B2 | 4/2014 | Jacobsen et al. | |
| 8,952,869 | B1* | 2/2015 | Weaver | G09G 5/00 |
| | | | | 345/8 |
| 2002/0140562 | A1* | 10/2002 | Gutta | G08B 21/06 |
| | | | | 340/576 |
| 2005/0046953 | A1* | 3/2005 | Repetto | G02B 27/017 |
| | | | | 359/630 |
| 2005/0073136 | A1* | 4/2005 | Larsson | A61B 3/113 |
| | | | | 280/735 |
| 2005/0156817 | A1* | 7/2005 | Iba | G02B 27/0093 |
| | | | | 345/8 |
| 2007/0057781 | A1* | 3/2007 | Breed | B60K 35/00 |
| | | | | 340/457.1 |
| 2008/0266552 | A1* | 10/2008 | Malawey | A61B 5/18 |
| | | | | 356/138 |
| 2008/0278821 | A1* | 11/2008 | Rieger | G02B 27/017 |
| | | | | 359/630 |
| 2010/0033333 | A1* | 2/2010 | Victor | A61B 3/113 |
| | | | | 340/576 |
| 2012/0139816 | A1* | 6/2012 | King | B60Q 9/00 |
| | | | | 345/7 |
| 2012/0229248 | A1 | 9/2012 | Parshionikar et al. | |
| 2012/0236025 | A1 | 9/2012 | Jacobsen et al. | |
| 2012/0268262 | A1* | 10/2012 | Popovic | B60Q 9/008 |
| | | | | 340/438 |
| 2012/0299950 | A1* | 11/2012 | Ali | G02B 27/0176 |
| | | | | 345/592 |
| 2013/0163825 | A1* | 6/2013 | Shimura | G06K 9/00335 |
| | | | | 382/107 |
| 2015/0102920 | A1* | 4/2015 | Sung | B60K 35/00 |
| | | | | 340/438 |
| 2015/0194035 | A1* | 7/2015 | Akiva | B60Q 9/00 |
| | | | | 340/575 |
| 2015/0294505 | A1* | 10/2015 | Atsmon | G06T 19/006 |
| | | | | 345/633 |
| 2015/0309311 | A1* | 10/2015 | Cho | G02B 27/017 |
| | | | | 345/8 |

* cited by examiner

HEAD-MOUNTED DISPLAY HEAD POSE AND ACTIVITY ESTIMATION

TECHNICAL FIELD

Aspects of the disclosure generally relate to head pose and activity estimation performed using a head-mounted display device worn by a vehicle driver.

BACKGROUND

A driver may be required to concentrate his or her gaze on the road and on various displays or controls of the vehicle. For example, content such as infotainment, phone integration, safety alerts, navigation displays, and driving efficiency may be displayed in various display screens throughout the vehicle cabin. In some cases, a driver may become fatigued, and may not be looking at the road or at displays of the vehicle providing information that would be useful to the driver.

SUMMARY

In a first illustrative embodiment, a system includes a processor configured to receive head pose indications determined according to movement data from a motion sensor of an optical head-mounted display worn by a vehicle driver, determine, according to the head pose indications, driver activity characteristics indicative of a history of movement of the head of the driver, and send the driver activity characteristics to a driver-aware vehicle system configured to adjust driver notification based on the driver activity characteristics.

In a second illustrative embodiment, a system includes a processor configured to receive raw movement data from a motion sensor of an optical head-mounted display worn on a head of a vehicle driver, compute head velocity data based on the raw movement data, compute head displacement data based on the head velocity data, and update head pose indications indicative of head positioning upon determining that the head displacement data exceeds a predetermined threshold displacement.

In a third illustrative embodiment, a system includes a processor configured to receive movement data from a motion sensor of an optical head-mounted display worn on a head of a vehicle driver, determine head pose indications determined according to the movement data, determine, according to the head pose indications, driver activity characteristics indicative of a history of movement of the head, and adjust display of content provided in the optical head-mounted display according to the driver activity characteristics.

DETAILED DESCRIPTION

Figure 1:
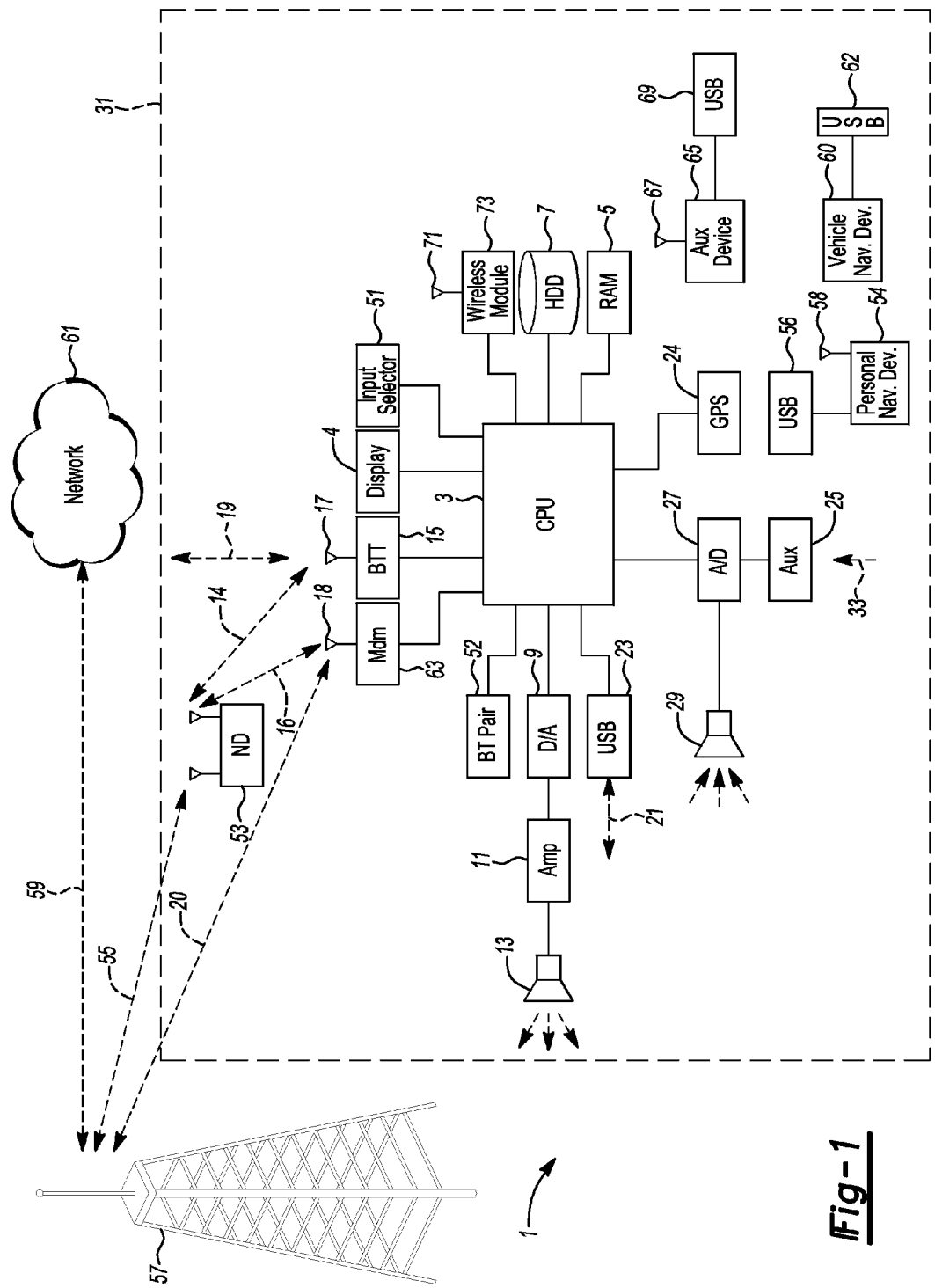
FIG. 1 illustrates an example block topology for a vehicle based computing system for a vehicle.

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Head position of a driver may be a useful clue into the gaze and state of the vehicle driver, as the head pose of the driver may be used to infer driver eye direction. Thus, a vehicle system may utilize head pose of a driver as a measure for driver attention estimation.

The vehicle system may be configured to measure driver head pose with non-intrusive or intrusive methods. Non-intrusive measurement techniques may include, for example, interior cameras and image processing performed based on captured images of the head of the driver. Intrusive methods may include, for example, head-mounted devices configured to more directly measure the orientation or location of the head of the driver. Intrusive methods of measuring driver gaze may be considered generally undesirable by drivers. However, for drivers who make use of a brought-in optical head-mounted display (OHMD), such as a Google Glass device already worn by the driver, the OHMD may be utilized by the vehicle systems for head pose estimation with respect to vehicle tasks.

Activities performed by the head of the driver (e.g., nodding, frequently looking over the shoulder, etc.) may be measured and utilized by the vehicle as inputs to processes such as driver state and workload estimation system. Those activities may be used to determine physical state of the driver (e.g., level of drowsiness) or driver workload and intention (e.g., lane change). As another example, as described in U.S. patent application Ser. No. 14/263,197 which is hereby incorporated by reference in its entirely, activities performed by the head of the driver may be utilized to inform a vehicle of which content to provide in which vehicle displays.

The OHMD may include motion sensors (e.g. accelerometer, gyroscope) that the vehicle system may utilize to provide information for estimating head pose and driver activity. In an example, the vehicle system may utilize a three-axis accelerometer of the OHMD to monitor motion of the OHMD mounted on the head of the driver (e.g., in the case of Google Glass, the motion sensor is located on the right hand corner of the device). The measured acceleration may then be translated into rotational motion and used to estimate driver head pose. In another example, the vehicle system may utilize the gyroscope of the OHMD to measure rotational motion of the driver head more directly. Further driver head pose and direction estimation may be determined by utilizing software sensors derived from the accelerometer and gyroscope sensors.

The vehicle system may be configured to estimate the head pose and activity of the driver by interfacing with a brought-in OHMD of the driver. This may accordingly allow the vehicle system to perform the driver estimation without requiring the vehicle to include non-intrusive measurement devices, or in combination with other non-intrusive measurement devices as a supplement measurement.

FIG. 1 illustrates an example block topology for a vehicle based computing system 1 (VCS) for a vehicle 31. An example of such a vehicle-based computing system 1 is the SYNC system manufactured by THE FORD MOTOR COMPANY. A vehicle enabled with a vehicle-based computing system may contain a visual front end interface 4 located in the vehicle. The user may also be able to interact with the interface if it is provided, for example, with a touch sensitive screen. In another illustrative embodiment, the interaction occurs through, button presses, spoken dialog system with automatic speech recognition and speech synthesis.

In the illustrative embodiment 1 shown in FIG. 1, a processor 3 controls at least some portion of the operation of the vehicle-based computing system. Provided within the vehicle, the processor allows onboard processing of commands and routines. Further, the processor is connected to both non-persistent 5 and persistent storage 7. In this illustrative embodiment, the non-persistent storage is random access memory (RAM) and the persistent storage is a hard disk drive (HDD) or flash memory. In general, persistent (non-transitory) memory can include all forms of memory that maintain data when a computer or other device is powered down. These include, but are not limited to, HDDs, CDs, DVDs, magnetic tapes, solid state drives, portable USB drives and any other suitable form of persistent memory.

The processor is also provided with a number of different inputs allowing the user to interface with the processor. In this illustrative embodiment, a microphone 29, an auxiliary input 25 (for input 33), a USB input 23, a GPS input 24, screen 4, which may be a touchscreen display, and a BLUETOOTH input 15 are all provided. An input selector 51 is also provided, to allow a user to swap between various inputs. Input to both the microphone and the auxiliary connector is converted from analog to digital by a converter 27 before being passed to the processor. Although not shown, numerous of the vehicle components and auxiliary components in communication with the VCS may use a vehicle network (such as, but not limited to, a CAN bus) to pass data to and from the VCS (or components thereof).

Outputs to the system can include, but are not limited to, a visual display 4 and a speaker 13 or stereo system output. The speaker is connected to an amplifier 11 and receives its signal from the processor 3 through a digital-to-analog converter 9. Output can also be made to a remote BLUETOOTH device such as PND 54 or a USB device such as vehicle navigation device 60 along the bi-directional data streams shown at 19 and 21 respectively.

In one illustrative embodiment, the system 1 uses the BLUETOOTH transceiver 15 to communicate 17 with a user's nomadic device 53 (e.g., cell phone, smart phone, PDA, or any other device having wireless remote network connectivity). The nomadic device can then be used to communicate 59 with a network 61 outside the vehicle 31 through, for example, communication 55 with a cellular tower 57. In some embodiments, tower 57 may be a WiFi access point.

Exemplary communication between the nomadic device and the BLUETOOTH transceiver is represented by signal 14.

Pairing a nomadic device 53 and the BLUETOOTH transceiver 15 can be instructed through a button 52 or similar input. Accordingly, the CPU is instructed that the onboard BLUETOOTH transceiver will be paired with a BLUETOOTH transceiver in a nomadic device.

Data may be communicated between CPU 3 and network 61 utilizing, for example, a data-plan, data over voice, or DTMF tones associated with nomadic device 53. Alternatively, it may be desirable to include an onboard modem 63 having antenna 18 in order to communicate 16 data between CPU 3 and network 61 over the voice band. The nomadic device 53 can then be used to communicate 59 with a network 61 outside the vehicle 31 through, for example, communication 55 with a cellular tower 57. In some embodiments, the modem 63 may establish communication 20 with the tower 57 for communicating with network 61. As a non-limiting example, modem 63 may be a USB cellular modem and communication 20 may be cellular communication.

In one illustrative embodiment, the processor is provided with an operating system including an API to communicate with modem application software. The modem application software may access an embedded module or firmware on the BLUETOOTH transceiver to complete wireless communication with a remote BLUETOOTH transceiver (such as that found in a nomadic device). Bluetooth is a subset of the IEEE 802 PAN (personal area network) protocols. IEEE 802 LAN (local area network) protocols include WiFi and have considerable cross-functionality with IEEE 802 PAN. Both are suitable for wireless communication within a vehicle. Another communication means that can be used in this realm is free-space optical communication (such as IrDA) and non-standardized consumer IR protocols.

In another embodiment, nomadic device 53 includes a modem for voice band or broadband data communication. In the data-over-voice embodiment, a technique known as frequency division multiplexing may be implemented when the owner of the nomadic device can talk over the device while data is being transferred. At other times, when the owner is not using the device, the data transfer can use the whole bandwidth (300 Hz to 3.4 kHz in one example). While frequency division multiplexing may be common for analog cellular communication between the vehicle and the internet, and is still used, it has been largely replaced by hybrids of Code Domain Multiple Access (CDMA), Time Domain Multiple Access (TDMA), Space-Domain Multiple Access (SDMA) for digital cellular communication. These are all ITU IMT-2000 (3G) compliant standards and offer data rates up to 2 mbs for stationary or walking users and 385 kbs for users in a moving vehicle. 3G standards are now being replaced by IMT-Advanced (4G) which offers 100 mbs for users in a vehicle and 1 gbs for stationary users. If the user has a data-plan associated with the nomadic device, it is possible that the data-plan allows for broad-band transmission and the system could use a much wider bandwidth (speeding up data transfer). In still another embodiment, nomadic device 53 is replaced with a cellular communication device (not shown) that is installed to vehicle 31. In yet another embodiment, the ND 53 may be a wireless local area network (LAN) device capable of communication over, for example (and without limitation), an 802.11g network (i.e., WiFi) or a WiMax network.

In one embodiment, incoming data can be passed through the nomadic device via a data-over-voice or data-plan, through the onboard BLUETOOTH transceiver and into the vehicle's internal processor 3. In the case of certain temporary data, for example, the data can be stored on the HDD or other storage media 7 until such time as the data is no longer needed.

Additional sources that may interface with the vehicle include a personal navigation device 54, having, for example, a USB connection 56 and/or an antenna 58, a vehicle navigation device 60 having a USB 62 or other connection, an onboard GPS device 24, or remote navigation system (not shown) having connectivity to network 61. USB is one of a class of serial networking protocols. IEEE 1394 (FireWire™ (Apple), i.LINK™ (Sony), and Lynx∩ (Texas Instruments)), EIA (Electronics Industry Association) serial protocols, IEEE 1284 (Centronics Port), S/PDIF (Sony/Philips Digital Interconnect Format) and USB-IF (USB Implementers Forum) form the backbone of the device-device serial standards. Most of the protocols can be implemented for either electrical or optical communication.

Further, the CPU could be in communication with a variety of other auxiliary devices 65. These devices can be connected through a wireless 67 or wired 69 connection. Auxiliary device 65 may include, but are not limited to, personal media players, wireless health devices, portable computers, and the like.

Also, or alternatively, the CPU could be connected to a vehicle based wireless router 73, using for example a WiFi (IEEE 803.11) 71 transceiver. This could allow the CPU to connect to remote networks in range of the local router 73.

In addition to having exemplary processes executed by a vehicle computing system located in a vehicle, in certain embodiments, the exemplary processes may be executed by a computing system in communication with a vehicle computing system. Such a system may include, but is not limited to, a wireless device (e.g., and without limitation, a mobile phone) or a remote computing system (e.g., and without limitation, a server) connected through the wireless device. Collectively, such systems may be referred to as vehicle associated computing systems (VACS). In certain embodiments particular components of the VACS may perform particular portions of a process depending on the particular implementation of the system. By way of example and not limitation, if a process has a step of sending or receiving information with a paired wireless device, then it is likely that the wireless device is not performing the process, since the wireless device would not "send and receive" information with itself. One of ordinary skill in the art will understand when it is inappropriate to apply a particular VACS to a given solution. In all solutions, it is contemplated that at least the vehicle computing system (VCS) located within the vehicle itself is capable of performing the exemplary processes.

Figure 2:
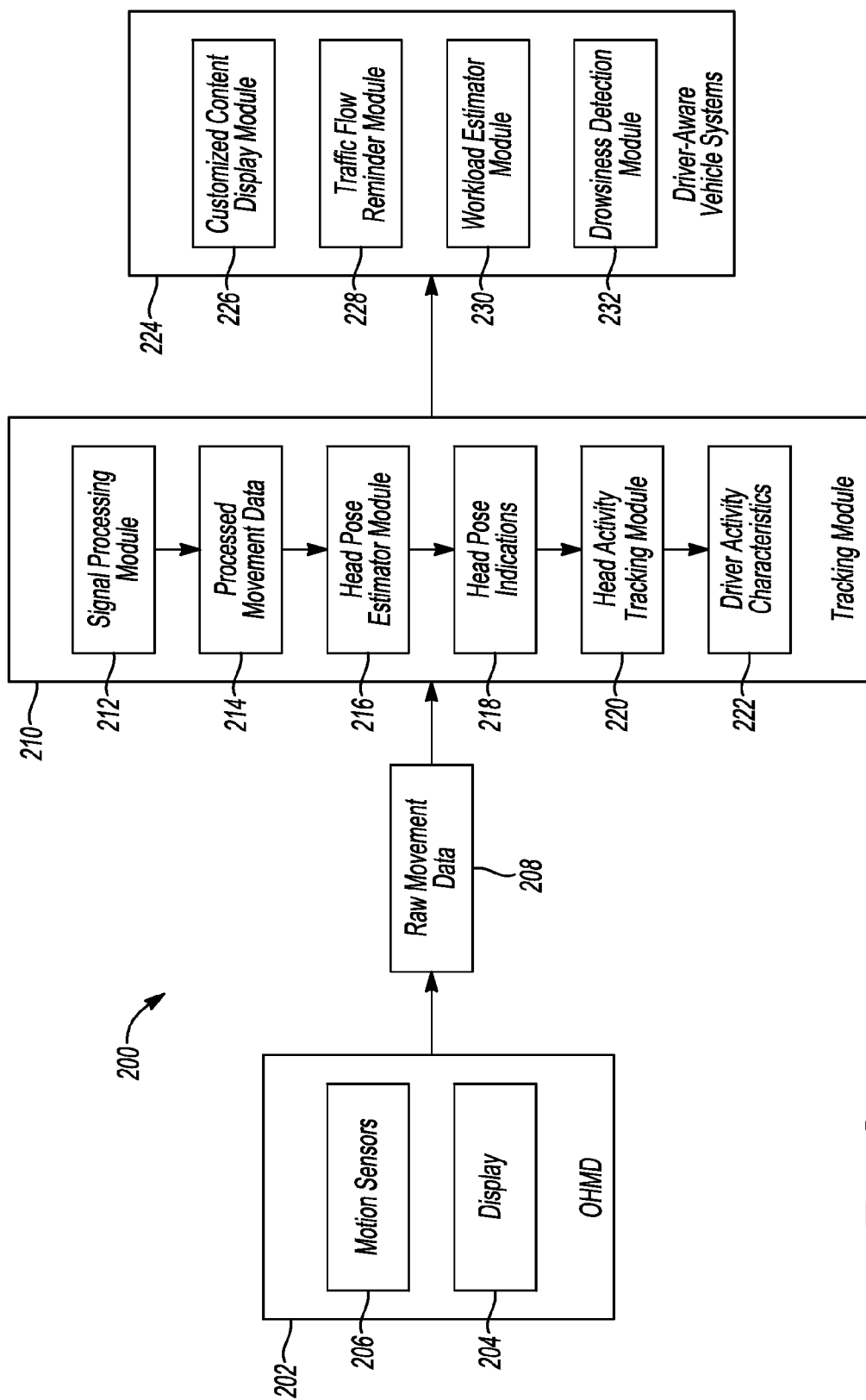
FIG. 2 illustrates an example block diagram of a system for head pose estimation and activity tracking.

FIG. 2 illustrates an example block diagram 200 of a system for head pose estimation and activity tracking. The modules of the exemplary system may be implemented by one or more processors or microprocessors of the vehicle 31 (such as the CPU 3 of the VCS 1) configured to execute firmware or software programs stored on one or more memory devices of the vehicle 31 (such as the storage 5 and 7). As illustrated, the system includes an OHMD 202 in communication with a tracking module 210. The OHMD 202 may include one or more displays 204 for providing information to a wearer of the OHMD 202, and one or more motion sensors 206 for tracking movements of the wearer. The tracking module 210 may include a signal processing module 212 configured to process raw movement data 208 captured from the motion sensors 206 into processed movement data 214, a head pose estimator module 216 configured to receive the processed movement data 214 and determine head pose indications 218, and a head activity tracking module 220 configured to receive the head pose indications 218 and track the gaze of the driver to determine driver activity characteristics 222. The system may include one or more additional driver-aware vehicle systems 224 configured to utilize the driver activity characteristics 222, such as a customized content display module 226, a traffic flow reminder module 228, a workload estimator module 230, and a driver drowsiness module 232, as some examples. It should be noted that the modularization illustrated in the diagram 200 is exemplary, and other arrangements or combinations of elements including more, fewer, or differently separated modules may be used.

The OHMD 202 may be one of various types of wearable device configured to be worn by a user to provide augmented reality information. In many cases, the OHMD 202 may be a brought-in device, meaning that the OHMD 202 is brought into the vehicle by the wearer of the device (e.g., the driver of the vehicle 31). In an example, the OHMD 202 may be a Google Glass device work by the driver of the vehicle 31.

The OHMD 202 may include one or more displays 204 configured to reflect projected images as well as allowing the wearer to see through it. The OHMD 202 may further include one or more motion sensors 206 (e.g., to allow the OHMD 202 to provide information in the displays 204 that adjusts according to movements of the wearer). The motion sensors 206 may include, for example, accelerometer sensors or gyroscopic sensors. In an example, the OHMD 202 may include a three-axis accelerometer motion sensor 206 to monitor motion of the head of the wearer in three dimensions. In another example, the OHMD 202 may utilize the gyroscope motion sensors 206 to measure rotational motion of the head of the wearer more directly than by measuring acceleration.

The raw movement data 208 may include signals received from the motion sensors 206 of the OHMD 202. In some examples, the raw movement data 208 may be in the form of acceleration measurements provided in meters per second squared ($m/s^2$), although other units data formats are possible. The raw movement data 208 may include noise due to small movements of the wearer. The raw movement data 208 may also include significant bias (e.g., a downward bias in gravitational acceleration in the y-axis).

The tracking module 210 may be configured to receive the raw movement data 208 from the OHMD 202, and utilize the raw movement data 208 for head pose estimation and activity tracking. To receive the raw movement data 208, the tracking module 210 may be configured to connect to the OHMD 202, and once connected, poll the OHMD 202 for data and/or receive periodic updates from the OHMD 202 over the connection. In an example, the connection between the tracking module 210 and the OHMD 202 may be over a BLUETOOTH connection between the OHMD 202 and the BLUETOOTH transceiver 15 of the VCS 1 of the vehicle 31, although other configurations are possible.

The signal processing module 212 of the tracking module 210 may be configured to process the raw movement data 208 captured from the motion sensors 206 for use by the tracking module 210 in head pose estimation and activity tracking. For example, the signal processing module 212 may be configured to filter the raw movement data 208 to obtain displacements and to remove drifting. The raw movement data 208 as processed by the signal processing module 212 may be referred to as processed movement data 214. The processed movement data 214 may accordingly include displacement data relating to the measured movement of the head of the wearer.

The head pose estimator module 216 may be configured to receive the processed movement data 214 from the signal processing module 212 and determine information regarding the wearer based on the received processed movement data 214. In an example, the head pose estimator module 216 may accordingly utilize the processed movement data 214 to estimate position and motion of the head of the wearer, such as turns of the head.

Based on the processed movement data 214, the head pose estimator module 216 may be configured to determine a head pose indication 218. As one example, the head pose indication 218 may include an indication of head position along the x-axis (e.g., whether the head is positioned to view left, right, or center). Additionally or alternately, the head pose indication 218 may include an indication of head position along the y-axis (e.g., whether the head is positioned upward, centered, or downward). Additionally or alternately, the head pose indication 218 may include an indication of head position along the z-axis (e.g., whether the head is positioned forward, centered, or backward). The head pose estimator module 216 may further be configured to utilize thresholds set to define the thresholds for which the head pose indications 218 may be identified (e.g., angles at which a driver is determined to be looking left, right, up, or down).

In some cases, the head pose estimator module 216 may further consider additional data for use in determining the head pose indications 218. In an example, the head pose estimator module 216 may further receive data from non-intrusive measurement techniques such as interior cameras and image processing performed based on captured images of the head of the driver.

The head activity tracking module 220 may be configured to receive the head pose indications 218 and track the gaze of the driver to determine driver activity characteristics 222. The driver activity characteristics 222 may include, for example, frequency and/or magnitude of driver head movements. As the driver activity characteristics 222 may provide an indication of the movements of the head of the driver over time, the driver activity characteristics 222 may be utilized to aid in a determination of physical state or workload of the driver.

The tracking module 210 may be configured to provide the head pose indications 218 and driver activity characteristics 222 to various driver-aware vehicle systems 224. The driver-aware vehicle systems 224 may include various systems of the vehicle 31 configured to adjust their operation based on the driver activity characteristics. As one example, the tracking module 210 may be configured to provide the head pose indications 218 as an input to a customized content display module 226, to inform driver gaze determination (e.g., to infer driver eye direction) for identifying which vehicle 31 displays should include what vehicle 31 content. As another example, the head pose indications 218 and driver activity characteristics 222 may be utilized as an input to a traffic flow reminder module 228 to aid in the determination of traffic flow reminders for a driver. As yet a further example, the head pose indications 218 and driver activity characteristics 222 may be utilized as a supplemental input to a workload estimator module 230, to allow the workload estimator module 230 to account for potentially increased driver workload that may be suggested by increased or particular head movements. As yet another example, the head pose indications 218 and driver activity characteristics 222 may be utilized as a supplemental input to a driver drowsiness module 232, to allow for consideration of the frequency of up and down motion of the driver's head (e.g., nodding off) in comparison to a predefined threshold indicative of likely driver drowsiness.

Figure 3:
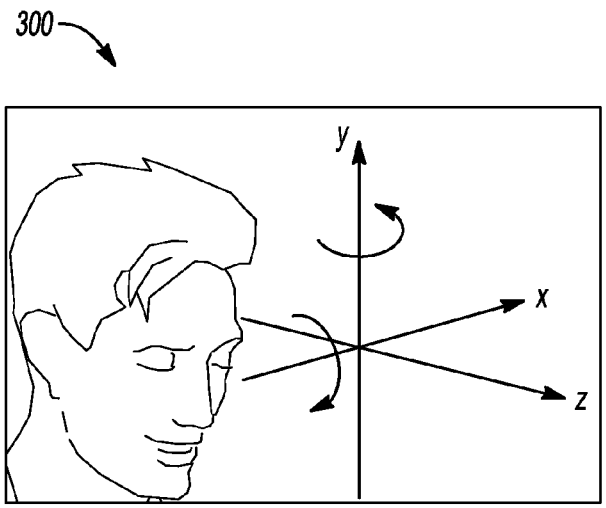
FIG. 3 illustrates an example head pose and coordinate system that may be used by the motion sensor of the optical head mounted display.

FIG. 3 illustrates an example head pose and coordinate system 300 that may be used by the motion sensor 206 of the OHMD 202. As illustrated, the x-axis may refer to the side to side turning of the head of the wearer, the y-axis may refer to the upward and downward movement of the head of the wearer, and the z-axis may refer to the forward and backward tilt of the head of the wearer. It should be noted that the illustrated coordinate system is merely an example, and other coordinate systems may be used.

Figure 4:
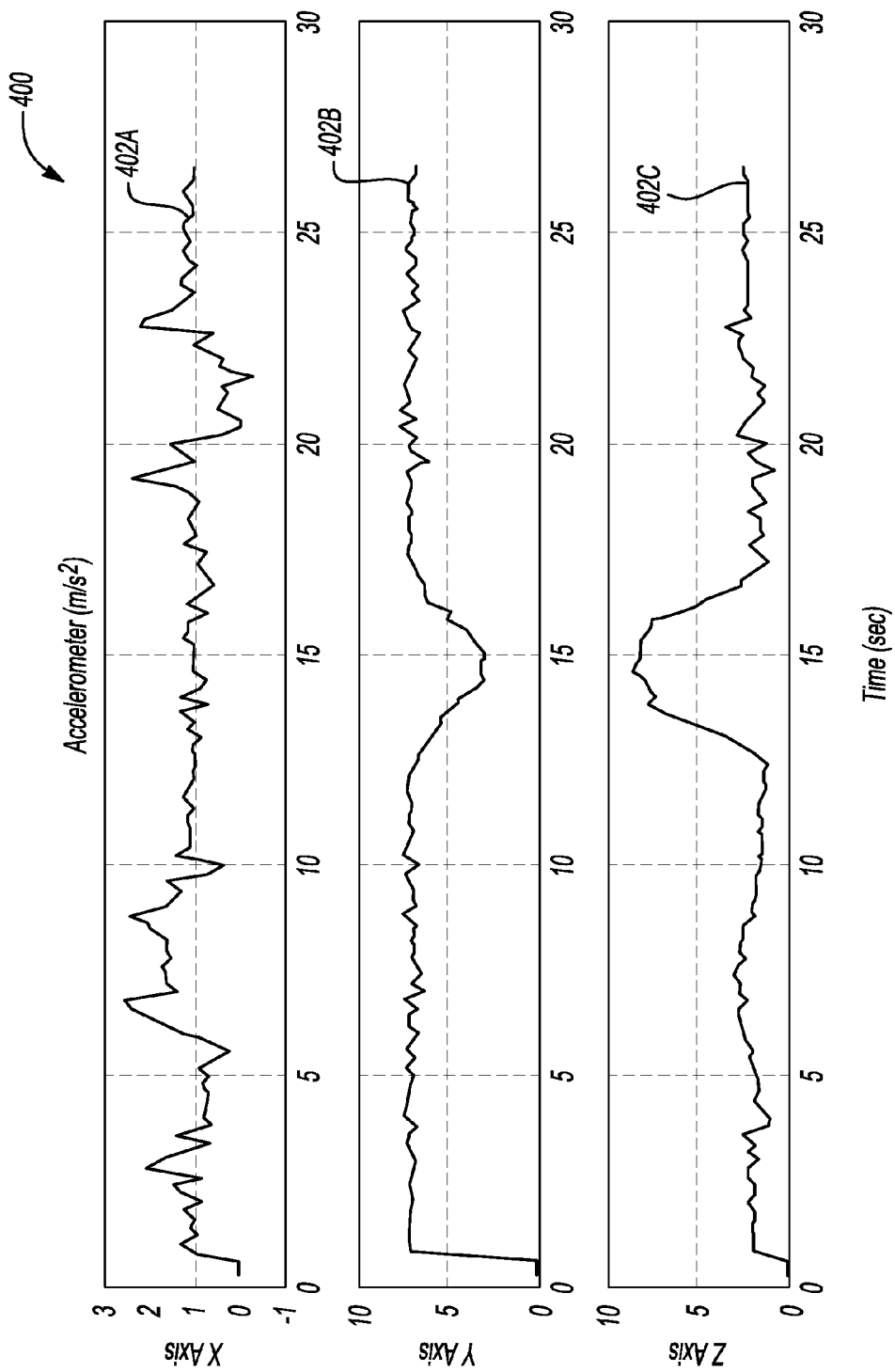
FIG. 4 illustrates an example of three-axis accelerometer raw movement data for the motion sensor of the optical head mounted display.

FIG. 4 illustrates an example 400 of three-axis accelerometer raw movement data 208 for the motion sensor 206 of the OHMD 202. The raw movement data is illustrated in the example head pose and coordinate system 300 data discussed above, including graphed data 402-A in the x-axis, graphed data 402-B in the y-axis, and graphed data 402-C in the z-axis (collectively graphed data 402). Regarding the content of the graphed data 402, the raw movement data 208 illustrates a sequence of head motion in the coordinate system 300, which includes a look to the left, followed by a look to the right down, followed by a look to the right. As illustrated in the graphed data 402-C, the raw movement data 208 includes a relatively significant bias in downward acceleration in y-axis due to the influence of gravity.

Figure 5:
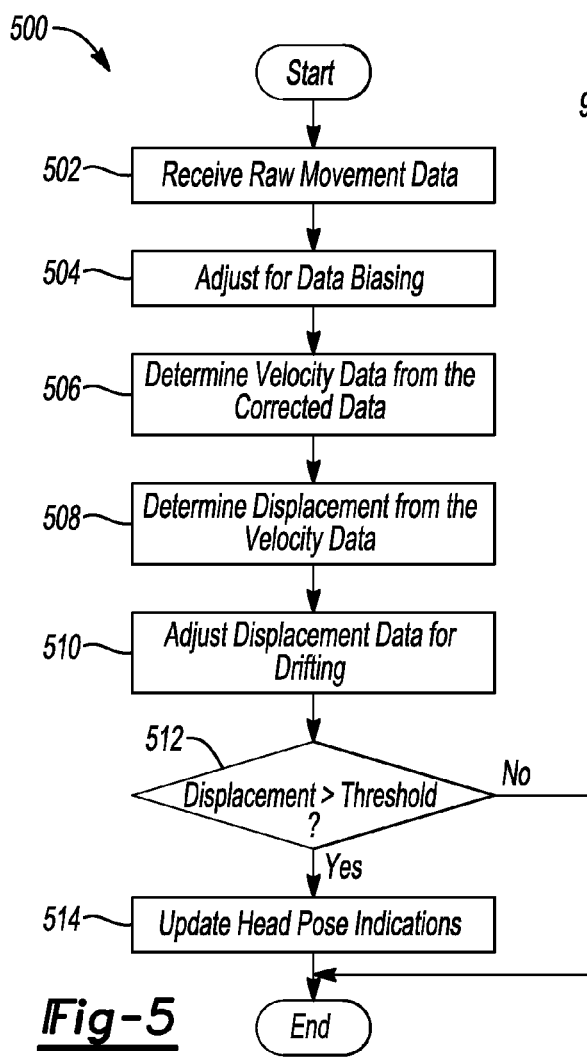
FIG. 5 illustrates an example process for head pose estimation of a driver wearing the optical head mounted display.

FIG. 5 illustrates an example process 500 for head pose estimation of a driver wearing the OHMD 202. The process 500 may be performed, for example, by the tracking module 210 of a vehicle 31 in communication with an OHMD 202 brought into and worn by a driver of the vehicle 31.

At operation 502, the tracking module 210 receives raw movement data 208. For example, the tracking module 210 may receive raw movement data 208 from the OHMD 202. An illustration of sample raw movement data 208 is shown above in the graphed data 402 of FIG. 4.

At operation 504, the tracking module 210 adjusts the raw movement data 208 for bias. For example, the signal processing module 212 of the tracking module 210 may receive the raw movement data 208 and perform a high-pass filtering on the raw movement data 208. The high-pass filtering may be performed, for example, to remove downward bias in the y-axis of the raw movement data 208 due to the influence of gravity. In an example, the high-pass filtering may be modeled according to an equation of the form: $y_i = \alpha \cdot (y_{i-1} + x_i - x_{i-1})$, where x is the raw movement data 208 input, y is the filtered output and a is a configurable time constant with respect to the time period of the integration.

At operation 506, the tracking module 210 determines velocity information from the adjusted raw movement data 208. For example, the tracking module 210 may perform an integration of the raw movement data 208 over time to determine the velocity information relating to the movement of the wearer of the OHMD 202.

At operation 508, the tracking module 210 determines displacement information from the velocity information determined in operation 506. For example, the tracking module 210 may perform a second integration over time of movement data 208 integrated in operation 506 to determine the displacement information relating to the movement of the wearer of the OHMD 202.

At operation 510, the tracking module 210 adjusts the displacement information to account for drifting. For example, the tracking module 210 may perform a second high-pass filtering of the raw movement data 208 similar to as performed above in operation 504. Accordingly, the calculated displacement information may provide the tracking module 210 with an approximation of the movement of the wearer of the OHMD 202.

Figure 6:
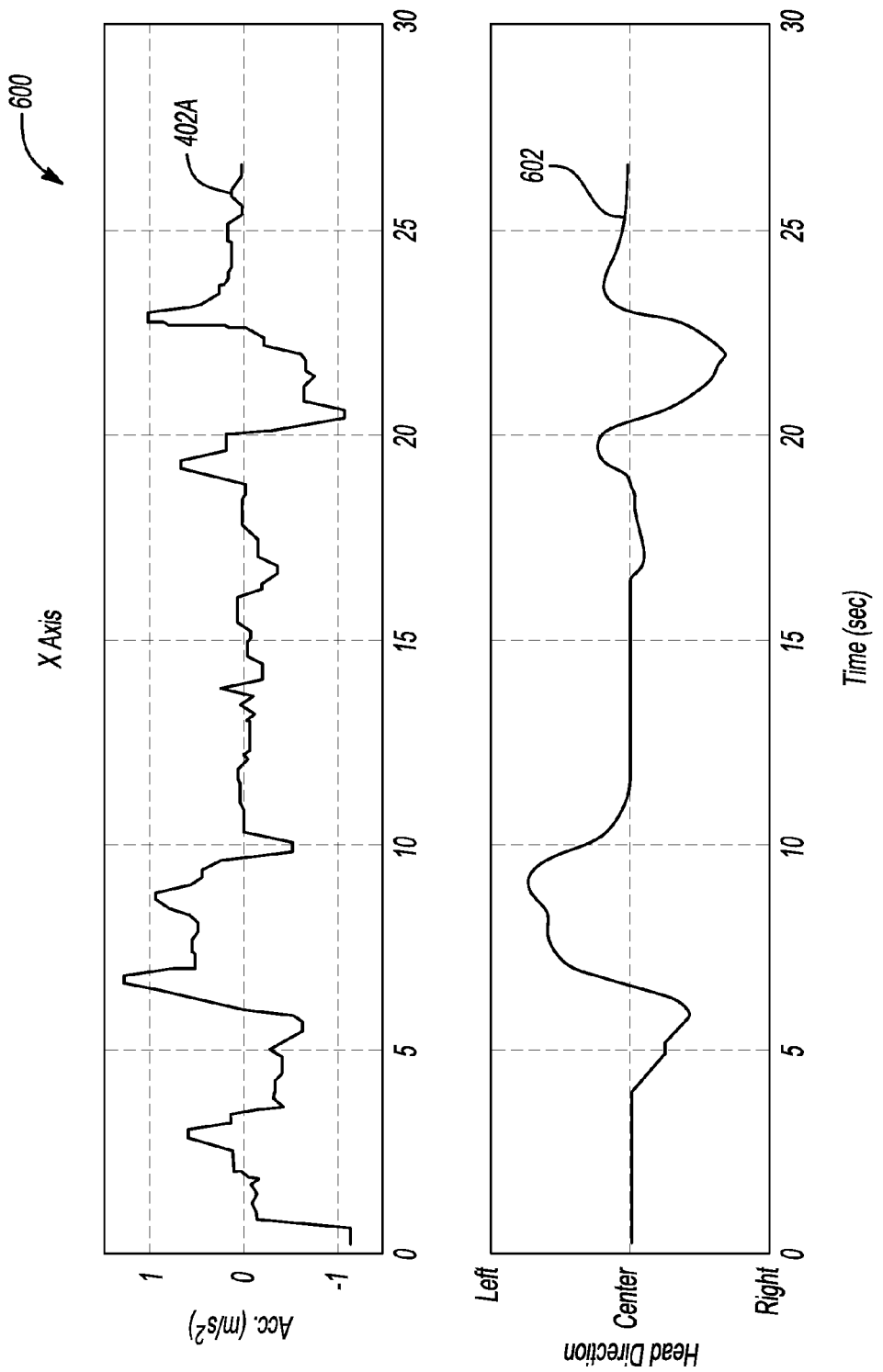
FIG. 6 illustrates an example head pose estimation in x-axis.

FIG. 6 illustrates an example head pose estimation 600 in the x-axis. The estimation 600 includes graphed data 402-A in the x-axis of raw movement data 208 from the motion sensor 206 of the OHMD 202, along with the corresponding x-axis calculated displacement information 602. Notably, the x-axis calculated displacement information 602 illustrates yaw motion (left and right) of the head of the wearer of the OHMD 202.

Figure 7:
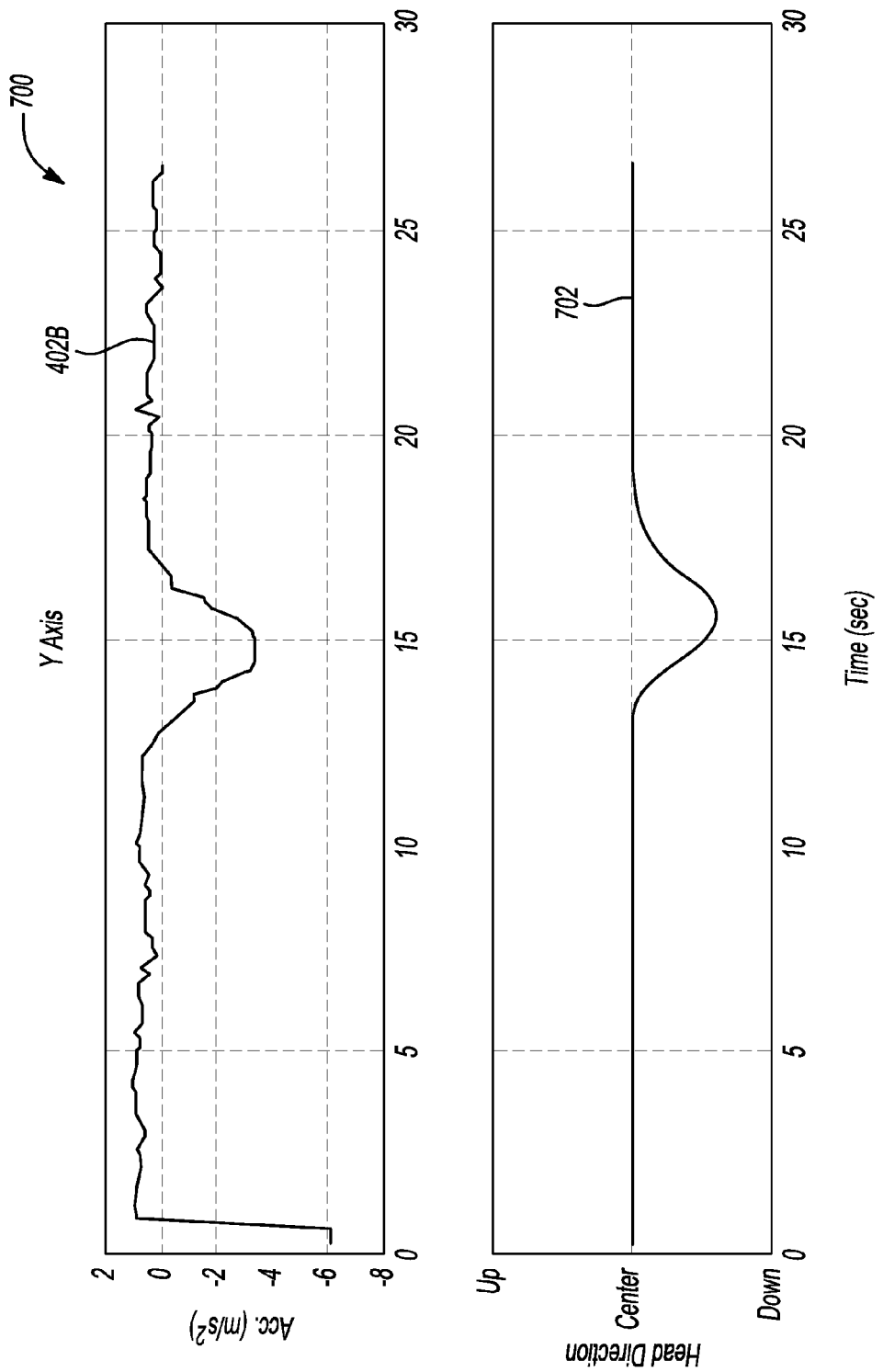
FIG. 7 illustrates an example head pose estimation in y-axis.

FIG. 7 illustrates an example head pose estimation 700 in the y-axis. The estimation 700 includes graphed data 402-B in the y-axis of raw movement data 208 from the motion sensor 206 of the OHMD 202, along with the corresponding y-axis calculated displacement information 702. Notably, the y-axis calculated displacement information 702 illustrates a downward movement of the head of the wearer of the OHMD 202.

Figure 8:
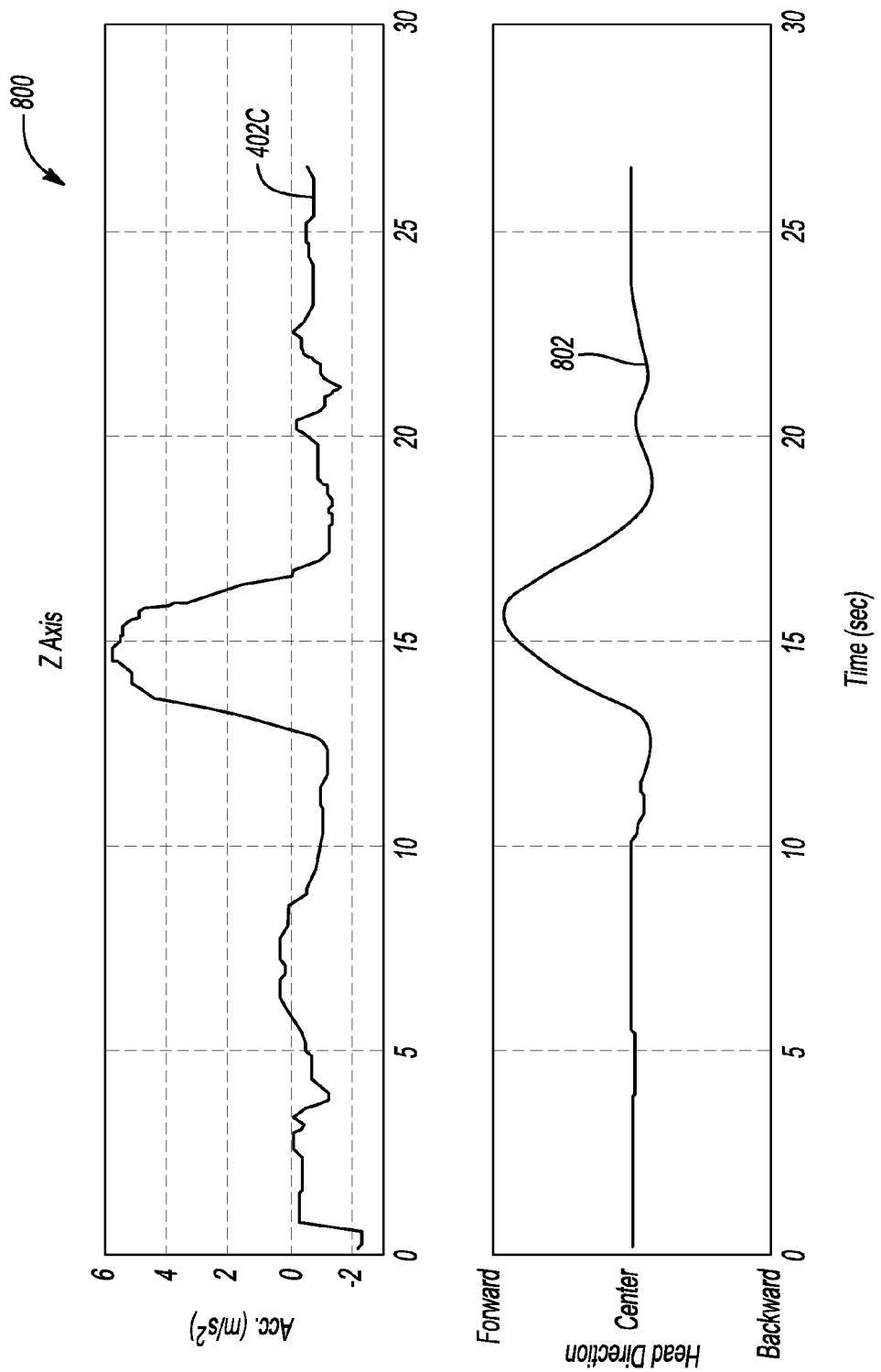
FIG. 8 illustrates an example head pose estimation in z-axis.

FIG. 8 illustrates an example head pose estimation 800 in the z-axis. The estimation 800 includes graphed data 402-C in the z-axis of raw movement data 208 from the motion sensor 206 of the OHMD 202, along with the corresponding z-axis calculated displacement information 802. Notably, the z-axis calculated displacement information 802 illustrates a forward movement of the head of the wearer of the OHMD 202.

Referring back to the process 500 of FIG. 5, at operation 512, the tracking module 210 determines whether the filtered displacement information exceeds a predetermined threshold amount of movement of the wearer. For example, the head pose estimator module 216 may receive the displacements determined in operation 510 by the signal processing module 212, and may compare the displacements to threshold values indicative of changes in current head pose of the wearer of the OHMD 202. In an example, the head pose estimator module 216 may compare displacements along an x-axis to x-axis thresholds, displacements along a y-axis to y-axis thresholds, and displacements along a z-axis to z-axis thresholds. If the head pose estimator module 216 determines that one or more of the displacements exceed a corresponding threshold, control passes to operation 514. Otherwise the process 500 ends.

At operation 514, the tracking module 210 updates head pose indications 218 of the wearer of the OHMD 202. As an example, the head pose estimator module 216 may generate one or more head pose indications 218 indicative of the one or more of the displacements that exceed a corresponding threshold. For instance, continuing with the example 400 of three-axis accelerometer raw movement data 208 for the motion sensor 206 of the OHMD 202, the head pose estimator module 216 may generate head pose indications 218 indicative of a look to the left, followed by a look to the right down, followed by a look to the right. Accordingly, the displacements determined in operation 510 may be used by the head pose estimator module 216 to determine the head pose indications 218 can be used to estimate the head turning motion. After operation 514, the process 500 ends.

Variations on the process 500 are possible. As one example, the head pose estimator module 216 may further consider additional data for use in improving accuracy of the head pose indications 218. In an example, the head pose estimator module 216 may further receive data from non-intrusive measurement techniques, such as interior cameras and image processing performed based on captured images of the head of the driver, to augment the data received from the OHMD 202.

Figure 9:
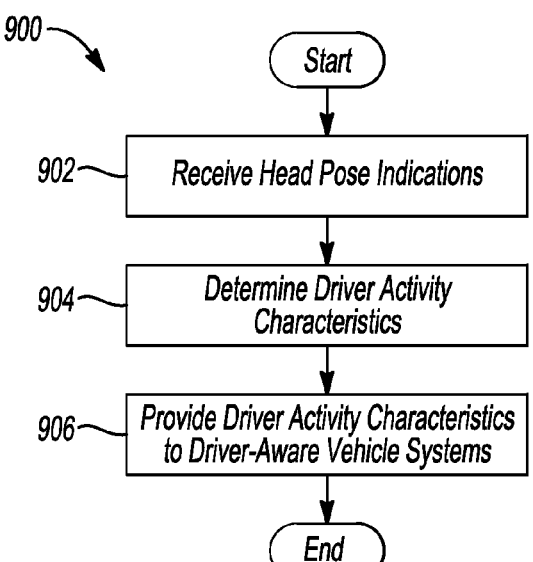
FIG. 9 illustrates an example process for using a head pose estimation determined according to the motion sensor of the optical head mounted display to inform systems of the vehicle of the status of the driver.

FIG. 9 illustrates an example process 900 for using a head pose estimation determined according to the motion sensor 206 of the OHMD 202 to inform systems of the vehicle 31 of the status of the driver. The process 900 may be performed, for example, by the tracking module 210 of a vehicle 31 in communication with other system of the vehicle 31, such as the driver-aware vehicle systems 224.

At operation 902, the tracking module 210 receives head pose indications 218 indicative of movements of the head of the wearer of the OHMD 202. In an example, the head pose indications 218 may be determined by the tracking module 210 in accordance with the process 500 discussed in detail above.

At operation 904, the tracking module 210 tracks the head pose indications 218 to determine driver activity characteristics 222. For example, the head activity tracking module 220 may, based on a history of the received head pose indications 218, determine driver activity characteristics 222 such as frequency and/or magnitude of driver head movements. As the driver activity characteristics 222 may provide an indication of the movements of the head of the driver over time, the driver activity characteristics 222 may be utilized to aid in a determination of physical state or workload of the driver.

At operation 906, the tracking module 210 provides the driver activity characteristics 222 to driver-aware vehicle systems 224. As one example, the tracking module 210 may be configured to provide the head pose indications 218 as an input to a customized content display module 226, to inform driver gaze determination (e.g., to infer driver eye direction) for identifying which vehicle 31 displays should include what vehicle 31 content. As another example, the head pose indications 218 and driver activity characteristics 222 may be utilized as an input to a traffic flow reminder module 228 to aid in the determination of traffic flow reminders for a driver. As yet a further example, the head pose indications 218 and driver activity characteristics 222 may be utilized as a supplemental input to a workload estimator module 230, to allow the workload estimator module 230 to account for potentially increased driver workload that may be suggested by increased or particular head movements. As yet another example, the head pose indications 218 and driver activity characteristics 222 may be utilized as a supplemental input to a driver drowsiness module 232, to allow for consideration of the frequency of up and down motion of the driver's head (e.g., nodding off) in comparison to a predefined threshold indicative of likely driver drowsiness.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A system comprising:
   a processor configured to
   store head pose indications, receive raw movement data from a motion sensor of an optical head-mounted display worn on a head of a vehicle driver, compute head velocity data based on the raw movement data, compute head displacement data based on the head velocity data, update the stored head pose indications indicative of head positioning upon determining that the head displacement data exceeds a predetermined threshold displacement, determine, according to the head pose indications over time, driver activity characteristics indicative of a history of frequency and magnitude of movement of the head of the driver, and send the driver activity characteristics to a driver-aware vehicle system configured to adjust driver workload notification settings based on driver-action previously observed with respect to the driver activity characteristics.

2. The system of claim 1, wherein the head pose indications are further determined according to information received from an in-vehicle camera monitoring the head of the driver.

3. The system of claim 1, wherein the driver-aware vehicle system includes a customized content display system configured to adjust display of content provided in the optical head-mounted display according to the driver activity characteristics.

4. The system of claim 1, wherein the driver-aware vehicle system includes a workload estimator configured to determine driver workload based on the driver activity characteristics.

5. The system of claim 1, wherein the driver-aware vehicle system includes a driver drowsiness module configured to estimate driver drowsiness based on the driver activity characteristics.

6. A system comprising:
a processor configured to
store head pose indications,
receive raw movement data from a motion sensor of an optical head-mounted display worn on a head of a vehicle driver,
compute head velocity data based on the raw movement data,
compute head displacement data based on the head velocity data, and
update the stored head pose indications indicative of head positioning upon determining that the head displacement data exceeds a predetermined threshold displacement.

7. The system of claim 6, wherein the processor is further configured to determine, according to the head pose indications, driver activity characteristics indicative of a history of movement of the head of the driver.

8. The system of claim 6, wherein the processor is further configured to perform a high-pass filter on the raw movement data to adjust for data bias before computing the head velocity data.

9. The system of claim 6, wherein the processor is further configured to perform a high-pass filter on the head displacement data to adjust for data bias before updating the head pose indications.

10. The system of claim 6, wherein the raw movement data includes indications of head position, and the head displacement data includes indications of head displacement along an x-axis of the head, a y-axis of the head, and a z-axis of the head.

11. The system of claim 10, wherein the predetermined threshold displacement includes at least one of a threshold displacement along the x-axis of the head, a threshold displacement along the y-axis of the head, and a threshold displacement along the z-axis of the head.

12. A system comprising:
a processor configured to
store head pose indications,
receive raw movement data from a motion sensor of an optical head-mounted display worn on a head of a vehicle driver,
compute head velocity data based on the raw movement data,
compute head displacement data based on the head velocity data,
update the stored head pose indications indicative of head positioning upon determining that the head displacement data exceeds a predetermined threshold displacement,
determine a history of head pose indications over time according to the movement data,
determine likely driver activity characteristics indicative of frequency and magnitude of driver head movement based on an observed history of the head pose indications, and
adjust driver workload according to the driver activity characteristics.

13. The system of claim 12, wherein the head pose indications are further determined according to information received from an in-vehicle camera monitoring the head of the driver.

14. The system of claim 12, wherein the movement data includes indications of head position, and the head pose indications includes indications of head positioning along an x-axis of the head, a y-axis of the head, and a z-axis of the head.

15. The system of claim 12, wherein the motion sensor includes at least one of an accelerometer sensor and a gyroscopic sensor.

16. The system of claim 12, wherein the processor is configured to receive the movement data from the motion sensor of the optical head-mounted display over a wireless connection between the optical head-mounted display and the processor.

* * * * *